United States Patent [19]

Beaurline

[11] Patent Number: 5,225,201
[45] Date of Patent: Jul. 6, 1993

[54] SALSALATE TABLET

[75] Inventor: Joseph M. Beaurline, North St. Paul, Minn.

[73] Assignee: Minnesota Mining and Manufacturing Company, St. Paul, Minn.

[21] Appl. No.: 748,977

[22] Filed: Aug. 23, 1991

[51] Int. Cl.$^5$ .................... A61K 9/20; A61K 31/235
[52] U.S. Cl. ................................ 424/465; 424/464; 424/499; 514/533
[58] Field of Search ............... 424/464, 465, 468, 470, 424/499

[56] References Cited

U.S. PATENT DOCUMENTS

| | | | |
|---|---|---|---|
| 4,308,251 | 12/1981 | Dunn et al. | 424/19 |
| 4,375,468 | 3/1983 | Dunn | 424/230 |
| 4,421,747 | 12/1983 | Ghyczy et al. | 424/199 |
| 4,457,907 | 7/1984 | Porter et al. | 424/7.1 |
| 4,639,458 | 1/1987 | Katdare | 514/311 |
| 4,649,204 | 3/1987 | Maryanoff | 548/541 |
| 4,666,716 | 5/1987 | Sheth et al. | 424/195.1 |
| 4,775,535 | 10/1988 | Lowey | 424/468 |
| 4,789,667 | 12/1988 | Makino et al. | 514/161 |
| 4,803,079 | 2/1989 | Hsiao et al. | 424/468 |
| 4,820,522 | 4/1989 | Radebaugh et al. | 424/468 |
| 4,828,836 | 5/1989 | Elger et al. | 424/419 |
| 4,867,979 | 9/1989 | Sheth et al. | 424/195.1 |

FOREIGN PATENT DOCUMENTS 8194812 11/1983 Japan.

OTHER PUBLICATIONS

Physicians Desk Reference, 1988, 42, 1678.
Acta Pharm. Suecica, 1984, 21, 1.

Primary Examiner—Thurman K. Page
Assistant Examiner—Neil Levy
Attorney, Agent, or Firm—Gary L. Griswold; Walter N. Kirn; Douglas E. Reedich

[57] ABSTRACT

A salsalate tablet containing hydroxypropyl cellulose as a binder substantially uniformly dispersed in the tablet. The tablet has good mechanical strength, exhibits a relatively low incidence of capping, and does not require a discrete outer film coating to prevent esophageal irritation.

15 Claims, No Drawings

SALSALATE TABLET

BACKGROUND OF THE INVENTION

1. Technical Field

This invention pertains to pharmaceutical tablet formulations. More particularly this invention pertains to tablets containing salsalate. In another aspect, this invention pertains to masking taste and esophageal irritation caused by pharmaceutical formulations, particularly tablets.

2. Description of the Related Art

Salsalate (salicylsalicylic acid; 2-hydroxybenzoic acid 2-carboxyphenyl ester) is a nonsteroidal anti-inflammatory drug (NSAID). Salsalate has a very unpleasant taste and causes irritation of the mucous membranes of the esophagus. Known salsalate tablets overcome this problem by either film coating or by including excipients in an amount great enough to mask the taste and irritation. For example, DISALCID ® (commercially available from Riker Laboratories, Inc., St. Paul, Minn.) is supplied as a tablet coated with hydroxypropyl methylcellulose and additionally containing magnesium stearate, microcrystalline cellulose, polyethylene glycol, polysorbate 80, starch, talc, and dye. *Physicians Desk Reference*, 1988, 42, 1678.

Salsalate is generally non-compressible and shows a wide variety of tableting characteristics depending on the method of manufacture. Salsalate tablets can be difficult to compress and may be subject to internal lamination, which may lead to a catastrophic tablet failure known as capping. Capping and its relation to axial and radial tensile strength are discussed in Acta Pharm. Suecica, 1984, 21, 1. Hydroxypropyl cellulose is a known pharmaceutic aid. It has been used as a binder, a film former, and as a granulating agent in both conventional and sustained release formulations. The use of hydroxypropyl cellulose in salsalate formulations is known. For example, U.S. Pat. No. 4,666,716 discloses an anti-diarrheal composition containing an NSAID such as salsalate and a polymeric hydroabsorptive agent in a ratio of between about 1:30 and about 1:600. The composition can be in the form of a tablet containing a binder such as hydroxypropyl cellulose. It is notable that these compositions contain the NSAID as a relatively minor component (i.e., at most several percent of the total weight of the composition).

U.S. Pat. No. 4,789,667 discloses pharmaceutical compositions comprising an effective amount of drug and an effective amount of a pyroglutamate as a skin-penetration enhancer. A variety of drugs, presentations, and excipients are disclosed. The composition can be in the form of a tablet, the drug can be an anti-inflammatory agent such as salsalate, and excipients in a tablet can include hydroxypropyl cellulose. The amounts of drug and excipient in a tablet are not addressed.

BRIEF DESCRIPTION OF THE INVENTION

This invention provides tablets containing salsalate, microcrystalline cellulose, hydroxypropyl cellulose as a binder substantially uniformly dispersed in the tablet, and a lubricant. Additional components incorporated in preferred embodiments include a conventional disintegrant such as a starch or a pre-gelatinized starch, or a disintegrant that is effective when used in a lesser quantity than that required when a conventional disintegrant is used. The latter class of disintegrants are referred to herein as superdisintegrants. A tablet of the invention exhibits at least about 85% dissolution when tested according to the dissolution assay set forth below.

One preferred embodiment of the invention provides a tablet comprising from about 80 to about 90 percent by weight salsalate, about 5 to about 15 percent by weight microcrystalline cellulose, about 1.5 to about 5.5 percent by weight hydroxypropyl cellulose, about 0.15 to about 0.5 percent by weight lubricant, and about 0.2 to about 1.5 percent by weight superdisintegrant, all weights being based on the total weight of the tablet.

A second embodiment provides a tablet comprising from about 81 to about 89 percent by weight salsalate, about 5 to about 12 percent by weight microcrystalline cellulose, about 1.1 to about 2.5 percent by weight hydroxypropyl cellulose, about 0.15 to about 0.4 percent by weight lubricant, and about 3.5 to about 8 percent by weight corn starch, all weights being based on the total weight of the tablet.

A third embodiment provides a tablet comprising from about 81 to about 85 percent by weight salsalate, about 13 to about 18 percent by weight microcrystalline cellulose, about 1 to about 5 percent by weight hydroxypropyl cellulose, and about 0.1 to about 0.5 percent lubricant, all weights being based on the total weight of the tablet.

Including hydroxypropyl cellulose in the tablets eliminates the need for a separately applied, discrete outer film coating, thus reducing production costs. Furthermore, the quantity of excipient is reduced, allowing a smaller tablet for a given dose relative to known tablets. Including hydroxypropyl cellulose also allows the salsalate to be formulated into tablets that have superior mechanical strength.

DETAILED DESCRIPTION OF THE INVENTION

The salsalate component of a tablet of this invention is preferably a powder. Preferably no more than about 1 percent of the salsalate particles are retained by a No. 20 sieve.

The microcrystalline cellulose component serves as a binder and as a disintegrant. Microcrystalline cellulose is described as purified, partially depolymerized cellulose prepared by treating alpha cellulose, obtained as a pulp from fibrous plant material, with mineral acids. National Formulary XV, p. 1218. A preferred microcrystalline cellulose is Avicel ™ PH101 microcrystalline cellulose (available from the FMC Corporation).

The hydroxypropyl cellulose component is substantially uniformly dispersed in the tablet and functions as a binder. It is thought that the hydroxypropyl cellulose becomes plastic under the pressures exerted by the conventional tableting apparatus used in the preparation of the tablet. Upon pressing, the hydroxypropyl cellulose flows to surround the salsalate. The resulting tablet, without a discrete outer coating, effectively masks the taste and esophageal irritation of the salsalate. The hydroxypropyl cellulose preferably has a molecular weight of between about 75,000 and about 125,000. A preferred hydroxypropyl cellulose is Klucel ™ LF hydroxypropyl cellulose (available from Hercules, Inc.).

The lubricant component can be any pharmaceutically acceptable lubricant. Such lubricants include silicone fluids, hydrogenated vegetable oils, microfine silica, stearate salts, stearic acid, polyethylene glycol, talc, sodium benzoate, sodium acetate, magnesium carbonate, magnesium oxide, and the like. The lubricant is present in an amount sufficient to provide acceptable die release properties to the tablets. The preferred lubricant is magnesium stearate.

The superdisintegrant component of a preferred tablet of the present invention can be any disintegrant that is effective when used in a substantially lesser quantity than that required when a conventional disintegrant is used. Examples of such superdisintegrants include crosslinked polyvinylpyrrolidone, sodium starch glycolate, and crosslinked carboxymethyl cellulose. The preferred superdisintegrant is a crosslinked sodium carboxymethyl cellulose known as croscarmellose sodium (Type A) (available from FMC Corporation under the trade designation Ac-Di-Sol TM).

The conventional disintegrant component is a common starch (e.g., corn starch) or a pregelatinized starch. Such materials can be obtained from any starch manufacturer such as, for example, the National Starch Corporation.

A preferred tablet of the present invention comprises from about 80 to about 90 percent, preferably about 84 percent, by weight salsalate; from about 5 to about 15 percent, preferably about 11.1 percent, by weight microcrystalline cellulose; about 1.5 to about 5.5 percent, preferably about 4 percent, by weight hydroxypropyl cellulose; about 0.15 to about 0.5 percent, preferably about 0.45 percent, by weight lubricant; and about 0.2 to about 1.5 percent, preferably about 0.7 percent, by weight superdisintegrant, all weights being based on the total weight of the tablet. Such tablets are prepared by granulating a preblended mixture of salsalate, microcrystalline cellulose, and superdisintegrant using a solution of about 10 to about 19 percent, preferably about 12 percent, hydroxypropyl cellulose in water as the granulating liquid. Alternatively, dry hydroxypropyl cellulose can be included in the preblend and water used as the granulating liquid. The granulation is dried until the loss-on-drying is less than 1%, then sized by oscillation through a 12 to 14 mesh screen. A portion, not more than about one-fourth, of the dried and sized granulation is mixed with the lubricant and this premix is then mixed with the remainder of the granulation. The lubricated granulation is compressed into tablets using conventional tablet presses.

Yet another embodiment of the present invention comprises from about 81 to about 89 percent, preferably about 84 percent, by weight salsalate; about 5 to about 12 percent, preferably about 6 percent, by weight microcrystalline cellulose; about 1.1 to about 2.5 percent, preferably about 2 percent, by weight hydroxypropyl cellulose, and about 0.15 to about 0.4 percent, preferably about 0.2 percent, by weight lubricant, and about 3.5 to about 8 percent, preferably about 8 percent, by weight corn starch; all weights being based on the total weight of the tablet. Tablets of this embodiment are prepared by granulating a preblended mixture of salsalate and corn starch using a solution of about 12 to about 19 percent hydroxypropyl cellulose in water as the granulating liquid. The granulation is dried until the loss-on-drying is less than 1%, then sized by oscillation through a 12 mesh screen. The dried, sized granulation is blended with the microcrystalline cellulose. A portion of the blend, not more than one-fourth, is mixed with the lubricant. This premix is blended with the remainder of the granulation. The lubricated granulation is compressed into tablets using conventional tablet presses.

Another embodiment of the invention comprises from about 81 to about 85 percent by weight salsalate, about 13 to about 18 percent by weight microcrystalline cellulose, about 1 to about 5 percent by weight hydroxypropyl cellulose, and about 0.1 to about 0.5 percent by weight lubricant, all weights being based on the total weight of the tablet. These tablets are made by granulating a preblended mixture of salsalate and microcrystalline cellulose using a solution of about 4 to about 6 percent hydroxypropyl cellulose in water as the granulating liquid. The granulation is dried and sized as described above. A portion is mixed with a lubricant and the resulting premix is put through a 12 mesh screen then mixed with the remainder of the granulation. The lubricated granulation is compressed into tablets using conventional tablet presses.

A tablet of the invention exhibits disintegration and dissolution properties consistent with conventional (i.e., rapid), not sustained, release of salsalate. A tablet of the invention exhibits at least about 85% dissolution when tested according to the dissolution assay set forth below (hereinafter referred to as the "Dissolution Assay"). For the purposes of the instant specification and claims, such dissolution values are the average of 6 independent determinations unless otherwise noted.

Preferably, tablets possess sufficient strength to withstand mechanical handling. One method of characterizing the mechanical strength of a tablet is by measuring the tensile strength. The ratio of the axial tensile strength to the radial tensile strength gives an isotropy ratio (G. Alderborn and C. Nystrom, Acta Pharmaceutic Suecica, 21, 1-8 (1984) incorporated herein by reference) or index of capping (P. Jarosz and E. Parrott, Journal of Pharmaceutical Sciences, 71, 607-614 (1982) incorporated herein by reference). The higher the value of the isotropy ratio the lesser the probability of capping. It is preferred that a tablet of the invention that has been compressed at a compression force of 2400 lbs exhibit a ratio of axial/radial tensile strength of at least about 0.25, more preferably at least about 0.3, and most preferably at least 0.4. Likewise, the higher the axial tensile strength, the lesser the probability of capping. It is preferred that a tablet of the invention that has been compressed at a compression force of 3300 lbs exhibit an axial tensile strength of at least about 3.0 kg/cm$^2$, more preferably at least about 4.0 kg/cm$^2$, and most preferably at least about 5.0 kg/cm$^2$. For the purposes of the instant specification and claims, all such values are the average values obtained for 10 tablets according to the test methods set forth below.

The following examples and tables are provided to illustrate the invention. The hydroxypropyl cellulose used in the examples was Klucel TM LF hydroxypropylcellulose from Hercules, Inc. The microcrystalline cellulose (MCC) used was Avicel TM PH101 microcrystalline cellulose. The croscarmellose sodium (Type A) was Ac-Di-Sol TM croscarmellose sodium. Salicylsalicylic acid is sometimes designated SSA. As used herein, friability means the friability measured on a Roche Friabilator for 20 tablets and 100 revolutions, and hardness means the average tablet hardness of ten tablets as measured on a Schleuniger Hardness Tester. Disintegration time, dissolution, axial tensile strength, and radial tensile strength are determined using the test methods described below.

Disintegration Time

The disintegration time is determined using a disintegration apparatus (USP XX) and USP gastric fluid without enzymes. 800 ml of simulated gastric fluid is placed in a 1 liter beaker. The beaker is placed in a constant temperature bath and the temperature of the fluid is allowed to reach 37±2° C. One tablet is placed in each of the 6 tubes of a basket. A disk is placed in each tube. The disk is oriented so that the flat surface with the greater area faces downward. The basket is positioned in the disintegration apparatus and the actuator is immediately started. The apparatus is operated at 37±2° C. The exact total elapsed time required for each tablet to disintegrate and completely pass through the screen is recorded. The disintegration time is the average of the time recorded for the 6 tablets.

Dissolution Assay

A dissolution apparatus conforming to the requirements for USP Apparatus 2 is used. 900 ml of 0.25M phosphate buffer solution having a pH of 7.4 is placed in a dissolution vessel. The paddle speed is set at 50 rpm and the dissolution medium is allowed to equilibrate to 37° C. One tablet is placed in the vessel. After 45 minutes a sample is withdrawn and analyzed for salicylsalicylic acid content using a UV spectrophotometer set at 308 nm. The amount of dissolved salicylsalicylic acid is reported as a percent of the claimed tablet salicylsalicylic acid content.

Axial Tensile Strength

The axial tensile strength of a tablet is measured as follows. A tablet is fastened between the heads of two ½ inch hex bolts using a thin coating of a quick set epoxy cement. The epoxied tablet is allowed to cure for 24 hours. The axial strength is measured by pulling the tablets apart using an Instron TM Model 1122 tensile testing machine equipped with a set of pneumatic jaws (crosshead speed at 5.0 mm/min). Only data from tablets that break in the body of the tablet are used. If the tablet breaks at the epoxy/bolt interface, the data are rejected. The calculation of $\sigma_A$ in kg/cm$^2$ from the Instron data is done using the following equation $$\sigma_A = \frac{4F}{\pi D^2}$$

where F is the force to pull the tablet apart in kg, and D is the diameter of the tablet in cm. The value reported is the average of the values obtained for ten tablets.

Radial Tensile Strength

The radial tensile strength of a tablet is measured using an Instron TM Model 1122 tensile testing machine using a crosshead speed of 5.0 mm/min. Only data from tablets that exhibit a tensile break are used. Calculation of the radial tensile strength $\sigma_R$ in kg/cm$^2$ is done using the equation below $$\sigma_R = \frac{2F_c}{\pi D t}$$

where $F_c$ is the force to crush the tablet in kg, D is the diameter of the tablet in cm, and t is the thickness of the tablet in cm. The value reported is the average of the values obtained for ten tablets.

EXAMPLE 1

Using a 20 quart Hobart mixer, 3,750 g of salicylsalicylic acid (SSA) powder was blended with 170 g of corn starch for 5 minutes at low speed (#1). 60.0 g of hydroxypropyl cellulose was dissolved in 294.4 g of water and the resulting solution was added to the SSA/corn starch blend with mixing. The mixture was granulated for 5 minutes then dried in a Glatt fluid bed drier for 45 min at 60° C. The granulation was then oscillated through a 12 mesh screen. The resulting granulation had a bulk density of 0.671 g/cc. Using a 12 quart Hobart mixer, 1,592 g of the granulation was blended with 100 g of Avicel TM PH101 microcrystalline cellulose at low speed for 5 minutes. Approximately one-fourth of this blend was placed in a plastic bag and mixed with 3.0 g of magnesium stearate (dense). The resulting premix was added to the remainder of the granulation in the Hobart mixer and mixed for 1 minute at speed #1. The granulation was compressed on a Stokes BB-2 press equipped with ½ inch flat faced beveled edged tooling and a tapered die using a compressive force of approximately 2900 pounds. The composition of the resulting tablets is shown in Table 1. The tablets were found to be nonirritating to the esophagus. The axial and radial tensile strengths were measured according to the methods described above.

TABLE 1

| Component | mg/tablet |
|---|---|
| Salicylsalicylic acid | 750.0 |
| Corn Starch | 34.0 |
| Hydroxypropyl cellulose | 12.0 |
| Microcrystalline cellulose | 50.0 |
| Magnesium stearate (dense) | 1.5 |
| Tensile Strength | |
| Axial tensile strength | 6.6 ± 1.3 kg/cm$^2$ |
| Radial tensile strength | 8.9 ± 0.9 kg/cm$^2$ |
| Axial/radial 0.74 | |

EXAMPLE 2

Using the general method of Example 1, tablets having the composition and tensile strengths shown in Table 2 were prepared. The hydroxypropyl cellulose was added as a 13.9% solution in water. The bulk density of the initial (before the addition of the microcrystalline cellulose and magnesium stearate) granulation was 0.618 g/cc. The tablets did not irritate the esophagus.

EXAMPLE 3

Using the general method of Example 1, tablets having the composition and tensile strengths shown in Table 2 were prepared. The hydroxypropyl cellulose was added as a 14.1% solution in water. The bulk density of the initial granulation was 0.654 g/cc. The tablets were found to be nonirritating to the esophagus.

EXAMPLE 4

Using the general method of Example 1, tablets with the composition and tensile strengths shown in Table 2 were prepared. The hydroxypropyl cellulose was added as a 18.1% solution in water. The bulk density of the initial granulation was 0.618 g/cc. The tablets did not irritate the esophagus.

EXAMPLE 5

Using the general method of Example 1, tablets having the composition and tensile strengths shown in Table 2 were prepared. The hydroxypropyl cellulose was added as a 15.7% solution in water. The bulk density of the initial granulation was 0.660 g/cc. The tablets did not irritate the esophagus.

TABLE 2

| | Example Number | | | |
|---|---|---|---|---|
| | 2 | 3 | 4 | 5 |
| Component | mg/tablet | | | |
| SSA | 750.0 | 750.0 | 750.0 | 750.0 |
| Corn Starch | 69.0 | 46.0 | 51.0 | 50.0 |
| HPC | 18.0 | 12.0 | 18.0 | 15.0 |
| MCC | 50.0 | 50.0 | 50.0 | 50.0 |
| Mg Stearate | 1.5 | 1.5 | 1.5 | 1.5 |
| Tensile Strengths | kg/cm$^2$ | | | |
| Axial | 8.8 ± 1.1 | 8.0 ± 1.0 | 9.5 ± 1.7 | 8.2 ± 1.2 |
| Radial | 11.1 ± 0.7 | 9.9 ± 0.6 | 11.1 ± 0.7 | 10.6 ± 0.6 |
| Axial/Radial | 0.79 | 0.81 | 0.86 | 0.77 |

EXAMPLE 6

Using a 12 quart Hobart mixer, 3,750 g of salicylsalicylic acid powder was blended with 250 g of corn starch at low speed for 5 minutes. A solution of 75.0 g of Klucel TM LF hydroxypropyl cellulose in 550 g of water was added while blending. The granulation time was 9.5 minutes. The granulation was dried in a fluid bed drier at 60° C. for 60 minutes then oscillated through a 12 mesh screen. The resulting granulation had a bulk density of 0.535 g/cc. Using a 12 quart Hobart mixer, 1728 g of the granulation was blended with 212.0 g of Avicel TM PH101 microcrystalline cellulose at low speed for 5 minutes. A portion (not more than one fourth) of the resulting granulation was placed in a plastic bag and mixed with 3.2 g of magnesium stearate (dense). The resulting premix was added to the remainder of the granulation in the mixer and blended at low speed for 1 minute. A portion of the granulation was compressed on a Stokes BB-2 press equipped with ½ inch flat faced beveled edged tooling and a tapered die using three different compressive forces. These tablets were used to measure axial and radial tensile strengths (Table 4). The remainder of the granulation was compressed on a Stokes BB-2 press equipped with 5/16 inch by ¾ inch standard cup upper bisect tooling and a tapered die. The composition of the tablets is shown in Table 3. These tablets were used to measure hardness, thickness, friability and dissolution (Table 4). Both types of tablets were found to be nonirritating to the esophagus.

TABLE 3

| Component | mg/tablet |
|---|---|
| Salicylsalicylic acid | 750.0 |
| Corn starch | 50.0 |
| Hydroxypropyl cellulose | 15.0 |
| Avicel TM PH101 microcrystalline cellulose | 100.0 |
| Magnesium stearate (dense) | 1.5 |

TABLE 4

| Compressive Force (lbs) | 1670 | 2400 | 3100 |
|---|---|---|---|
| Axial TS (kg/cm$^2$) | 20.0 | 18.2 | 23.8 |
| Radial TS (kg/cm$^2$) | 20.8 | 32.2 | 37.4 |
| Axial/Radial | 0.96 | 0.57 | 0.64 |
| Hardness (kp) | 10.6 ± 1.5 | 15.4 ± 2.2 | 19.1 ± 1.3 |
| Thickness (mm) | 7.03 ± 0.01 | 6.78 ± 0.02 | 6.62 ± 0.01 |
| Friability | 0.18% | 0.09% | 0.01% |
| Dissolution (average of 3 tablets) | 96.9% | 99.2% | 98.4% |

EXAMPLE 7

Using a 12 quart Hobart mixer, 750.0 g of salicylsalicylic acid powder was blended with 150.0 g of Avicel TM PH101 microcrystalline cellulose for 5 minutes at low speed. A solution of 19 0 g of Klucel TM LF hydroxypropyl cellulose in 380 g of water was added to the blended powders. The granulation time was 1 minute. The granulation was dried in a fluid bed drier for 45 minutes at 60° C. then oscillated through a 12 mesh screen. Approximately 200 g of the granulation was combined with 1.35 g of magnesium stearate (dense) in a glass jar, blended on a Turbula mixer at medium high speed for 30 seconds and then put through a 12 mesh screen. The resulting premix was blended with the remainder of the granulation in a Hobart mixer for 1 minute at low speed. A portion of the granulation was compressed on the Stokes BB-2 press equipped with ½ inch flat faced beveled edged tooling and a tapered die using a compressive force of about 3700 pounds. These tablets were used to measure tensile strengths (Table 5). The remainder of the granulation was compressed on a Stokes BB-2 press equipped with ¾ inch by 5/16 inch standard cup upper bisect tooling and a tapered die using a compressive force of either 2970 lbs. or 3690 lbs. These tablets were used to determine hardness, thickness, and friability (Table 5). Both types of tablets were found to be nonirritating to the esophagus.

TABLE 5

| Component | mg/tablet | |
|---|---|---|
| Salicylsalicylic acid | 750.0 | |
| MCC | 150.0 | |
| HPC | 19.0 | |
| Magnesium stearate (dense) | 1.5 | |
| Tensile strengths | kg/cm$^2$ | |
| Axial | 13.48 ± 3.47 | |
| Radial | 20.55 ± 0.68 | |
| Axial/Radial | 0.66 | |
| Compressive Force (lbs) | 2970 | 3690 |
| Hardness (kp) | 16.1 ± 1.4 | 19.1 ± 0.6 |
| Thickness (mm) | 6.48 ± 0.02 | 6.35 ± 0.02 |
| Friability | 0.05% | 0.07% |

EXAMPLE 8

A hydroxypropyl cellulose solution was prepared by slowly adding 480 g of Klucel TM LF hydroxypropyl cellulose to 4892 ml of water with stirring. The stirring was continued until dissolution was complete. 5000 g of salicylsalicylic acid powder, 665 g of Avicel TM PH101 microcrystalline cellulose and 40 g of Ac-Di-Sol TM crosscarmellose solution were placed in a Fuji vertical granulator equipped with a 35° triple blade and mixed for 5 minutes with the blade speed set at 300 rpm and the cross-screw set at low speed. The hydroxypropyl cellulose solution was added to the powder mass at a rate of 110 ml/min. The blade speed was set at 450 rpm and the cross-screw was set at high speed. After 17 minutes the powder mass still looked dry. The granulation process was continued with the blade speed reduced to 400 rpm then to 300 rpm. After 5 minutes, the mass appeared to be uniformly wetted. It was beaten for 1 minute with the blade speed at 150 rpm. The granulation was dried in a fluid bed drier at 60° C. until the loss-on-drying was less than 1%. The bulk density was 0.576 g/cc. 2378 g of the granulation was placed in a 12 quart Hobart mixer and blended with 4.0 g of magnesium stearate (dense) for 4 minutes at low speed (#1). The granulation was compressed on a Stokes BB-2 press equipped with ½ inch flat faced beveled edged tooling and a tapered die using three different compressive forces. The composition and axial and radial tensile strengths of the tablets are shown in Table 6. The tablets were found to be nonirritating to the esophagus.

TABLE 6

| Component | mg/tablet | | |
|---|---|---|---|
| Salicylsalicylic acid | 1000.0 | | |
| Avicel TM PH101 microcrystalline cellulose | 133.0 | | |
| Ac-Di-Sol TM croscarmellose sodium | 8.0 | | |
| Klucel TM LF Hydroxypropyl cellulose | 48.0 | | |
| Magnesium stearate (dense) | 2.0 | | |
| Compressive force (lbs) | 2400 | 3300 | 4200 |
| Axial TS (kg/cm²) | 3.5 ± 2.1 | 3.2 ± 2.6 | 5.5 ± 3.4 |
| Radial TS (kg/cm²) | 8.8 ± 1.0 | 11.6 ± 1.1 | 14.6 ± 1.0 |
| Axial/radial ratio | 0.40 | 0.28 | 0.38 |

EXAMPLE 9

5,000 g of salicylsalicylic acid powder, 665 g of Avicel TM PH101 microcrystalline cellulose, 40 g of Ac-Di-Sol TM croscarmellose sodium and 240 g of Klucel TM LF hydroxypropyl cellulose were placed in a Fuji vertical granulator and dry mixed for 5 minutes with the blade speed set at 300 rpm and the cross-screw at low speed. The blade speed was set to 450 rpm and the cross-screw to high speed then water was sprayed under 1 bar of pressure and delivered at a rate of about 200 ml per minute. After 8 minutes the mass still looked dry and not uniformly wetted. It was beaten for 2 minutes without spraying. The blade speed was reduced to 200 rpm and water sprayed for another minute. A total of 1600 ml of water was sprayed. The mass was beaten for 1 minute then discharged. The granulation was dried in a fluid bed drier at 60° C. until the loss-on-drying was less than 1% than oscillated through a 12 mesh screen. The bulk density was 0.593 g/cc. 2,378 g of the granulation was placed in a 20 quart Hobart mixer and blended with 4.0 g of magnesium stearate (dense) for 4 minutes at low speed (#1). The granulation was compressed on a Stokes BB-2 press equipped with ½ inch flat faced beveled edged tooling and a tapered die using three different compressive forces. The composition of the tablets and the axial and radial tensile strengths are shown in Table 7. The tablets did not irritate the esophagus.

TABLE 7

| Component | mg/tablet | | |
|---|---|---|---|
| Salicylsalicylic acid | 1000.0 | | |
| Avicel TM PH101 microcrystalline cellulose | 133.0 | | |
| Ac-Di-Sol TM croscarmellose sodium | 8.0 | | |
| Klucel TM LF Hydroxypropyl cellulose | 48.0 | | |
| Magnesium stearate (dense) | 2.0 | | |
| Compressive force (lbs) | 2400 | 3300 | 4200 |
| Axial TS (kg/cm²) | 2.9 ± 2.0 | 3.6 ± 2.8 | 3.8 ± 2.7 |
| Radial TS (kg/cm²) | 8.6 ± 0.7 | 11.5 ± 0.9 | 14.3 ± 0.9 |

TABLE 7-continued

| Axial/radial ratio | 0.34 | 0.31 | 0.27 |
|---|---|---|---|

EXAMPLE 10

A 20 quart bowl of a Hobart mixer was charged with 3,750 g of salicylsalicylic acid powder, 500.0 g of Avicel TM PH101 microcrystalline cellulose and 30.0 g of Ac-Di-Sol TM croscarmellose sodium. The powders were blended for 10 minutes at speed #1. 1,487 g of a 12.1% solution of Klucel TM LF hydroxypropyl cellulose was added while mixing at speed #1. The resulting mixture was granulated for 3.5 minutes. The granulation was dried in a fluid bed drier at 60° C. for 1 hour then oscillated through a 0.039 inch screen. 4173 g of the granulation was placed in a 20 quart bowl on a Hobart mixer. Approximately one fourth of the granulation was removed, placed in a plastic bag and mixed with 18.7 g of magnesium stearate (dense). This premix was added to the the remainder of the granulation in the Hobart bowl and blended for 1 minute at speed #1. A portion of the granulation was compressed on a Stokes BB-2 press equipped with flat faced beveled edged tooling and a tapered die at three different compressive forces. These tablets were used for the tensile strength measurements (Table 8). The remainder of the granulation was compressed on a Stokes BB-2 press equipped with 5/16 inch by ⅜ inch standard cup upper bisect tooling and a tapered die. These tablets were used in the determination of hardness, friability, disintegration, and dissolution. The tablets were found to be nonirritating to the esophagus. The composition and characteristics of the tablets are shown in Table 8.

TABLE 8

| Component | mg/tablet | | |
|---|---|---|---|
| Salicylsalicylic acid | 750.0 | | |
| Avicel TM PH101 microcrystalline cellulose | 100.0 | | |
| Ac-Di-Sol TM croscarmellose sodium | 6.0 | | |
| Klucel TM LF Hydroxypropyl cellulose | 36. | | |
| Magnesium stearate (dense) | 4.0 | | |
| Tablet Characteristics | | | |
| Hardness (kp) | 20 | | |
| Friability | 0.0% | | |
| Disintegration time (minutes) | 4.97 ± 1.08 | | |
| Dissolution (n = 6) | 96.2 ± 2.7% | | |
| Compressive force (lbs) | 2400 | 3300 | 4200 |
| Axial TS (kg/cm²) | 6.3 ± 4.1 | 6.6 ± 3.4 | 6.8 ± 3.8 |
| Radial TS (kg/cm²) | 13.6 ± 1.3 | 17.7 ± 1.6 | 20.4 ± 1.1 |
| Axial/radial ratio | 0.46 | 0.33 | 0.37 |

EXAMPLES 11-18

Using the general method of example 10, tablets with the composition and characteristics shown in Tables 9 and 10 were prepared. The tablets were formed on a Stokes BB-2 press equipped with ⅜ inch by 5/16 inch standard cup upper bisect tooling and a tapered die using three different compressive forces.

TABLE 9

| | | mg/tablet | | | |
|---|---|---|---|---|---|
| Example | SSA | Avicel TM | HPC | Ac-Di-Sol TM | MgSt |
| 11 | 750.0 | 100.0 | 30.0 | 4.0 | 4.0 |
| 12 | 750.0 | 100.0 | 42.0 | 4.0 | 4.0 |

TABLE 9-continued

| Example | SSA | mg/tablet Avicel ™ | HPC | Ac-Di-Sol ™ | MgSt |
|---|---|---|---|---|---|
| 13 | 750.0 | 100.0 | 30.0 | 8.0 | 4.0 |
| 14 | 750.0 | 100.0 | 42.0 | 8.0 | 4.0 |
| 15 | 750.0 | 100.0 | 36.0 | 2.0 | 4.0 |
| 16 | 750.0 | 100.0 | 36.0 | 10.0 | 4.0 |
| 17 | 750.0 | 100.0 | 26.0 | 6.0 | 4.0 |
| 18 | 750.0 | 100.0 | 46.0 | 6.0 | 4.0 |

SSA = salicylsalicylic acid; HPC = hydroxypropyl cellulose
MgSt = magnesium stearate

TABLE 10

| Compressive Force (lbs) | 2400 | 3300 | 4200 | 2400 | 3300 | 4200 |
|---|---|---|---|---|---|---|
| Example | Hardness (kp) | | | Dissolution (%) | | |
| 11 | 15.6 | 18.1 | 20.5 | 105.0[6] | * | 103.8[5] |
| 12 | 15.6 | 18.5 | 20.1 | 100.1[6] | * | 108.5[6] |
| 13 | 14.6 | 16.3 | 18.9 | 102.7[6] | * | 107.9[5] |
| 14 | 14.0 | 17.3 | 21.4 | 97.7[6] | * | 100.6[6] |
| 15 | 14.8 | 17.1 | * | * | 98.1[3] | 104.1[5] |
| 16 | 14.6 | 16.6 | 19.8 | * | 100[3] | * |
| 17 | 13.7 | 16.5 | 19.6 | * | 100[2] | * |
| 18 | 15.7 | 16.4 | 21.0 | * | 92.3[5] | * |

*Value not determined; the superscript indicates the number of tablets used to determine the value given.

What is claimed is:

1. A tablet comprising:
   a) about 80 to about 90 percent by weight salsalate based on the total weight of the tablet;
   b) about 5 to about 15 percent by weight microcrystalline cellulose based on the total weight of the tablet;
   c) as a binder, substantially uniformly dispersed in the tablet, in about 1.5 to about 5.5 percent by weight hydroxypropyl cellulose based on the total weight of the tablet;
   d) about 0.15 to about 0.5 percent by weight lubricant based on the total weight of the tablet; and
   e) about 0.2 to about 1.5 percent by weight super-disintegrant based on the total weight of the tablet,
   which tablet exhibits at least about 85% dissolution when tested according to the Dissolution Assay.

2. A tablet according to claim 1 wherein the super-disintegrant is croscarmellose sodium (Type A).

3. A tablet according to claim 1 wherein the hydroxypropyl cellulose has a molecular weight from about 75,000 to about 125,000.

4. A tablet according to claim 1 wherein the lubricant is magnesium stearate.

5. A tablet comprising:
   a) about 83.7 percent by weight salsalate based on the total weight of the tablet;
   b) about 11.2 percent by weight microcrystalline cellulose based on the total weight of the tablet;
   c) about 4 percent by weight hydroxypropyl cellulose based on the total weight of the tablet;
   d) about 0.45 percent by weight magnesium stearate based on the total weight of the tablet; and
   e) about 0.67 percent by weight croscarmellose sodium (type A) based on the total weight of the tablet.

6. A tablet according to claim 5, containing about 500 to about 1000 mg of salsalate.

7. A tablet comprising:
   a) about 81 to about 89 percent by weight salsalate based on the total weight of the tablet;
   b) about 5 to about 12 percent by weight microcrystalline cellulose based on the total weight of the tablet;
   c) as a binder, substantially uniformly dispersed in the tablet, about 1.1 to about 2.5 percent by weight hydroxypropyl cellulose based on the total weight of the tablet;
   d) about 0.15 to about 0.4 percent by weight lubricant based on the total weight of the tablet; and
   e) about 3.5 to about 8 percent by weight corn starch based on the total weight of the tablet,
   which tablet exhibits at least about 85% dissolution when tested according to the Dissolution Assay.

8. A tablet according to claim 7 wherein the hydroxypropyl cellulose has a molecular weight of from about 75,000 to about 125,000.

9. A tablet according to claim 7 wherein the lubricant is magnesium stearate.

10. A tablet comprising:
    a) about 84.4 percent by weight salsalate based on the total weight of the tablet;
    b) about 5.6 percent by weight microcrystalline cellulose based on the total weight of the tablet;
    c) about 2 percent by weight hydroxypropyl cellulose based on the total weight of the tablet;
    d) about 0.2 percent by weight magnesium stearate based on the total weight of the tablet; and
    e) about 7.8 percent by weight corn starch based on the total weight of the tablet.

11. A tablet according to claim 10, containing about 500 to about 1000 mg of salsalate.

12. A tablet comprising:
    a) about 81 to about 85 percent by weight salsalate based on the total weight of the tablet;
    b) about 13 to about 18 percent by weight microcrystalline cellulose based on the total weight of the tablet;
    c) as a binder, substantially uniformly dispersed in the tablet, about 1 to about 5 percent by weight hydroxypropyl cellulose based on the total weight of the tablet; and
    d) about 0.1 to about 0.5 percent by weight lubricant based on the total weight of the tablet,
    which tablet exhibits at least about 85% dissolution when tested according to the Dissolution Assay.

13. A tablet according to claim 12 wherein the hydroxypropyl cellulose has a molecular weight from about 75,000 to about 125,000.

14. A tablet according to claim 12 wherein the lubricant is magnesium stearate.

15. A tablet according to claim 12, containing about 500 to about 1000 mg of salsalate.

* * * * *

UNITED STATES PATENT AND TRADEMARK OFFICE
CERTIFICATE OF CORRECTION

PATENT NO. :   5,225,201

DATED      :   July 6, 1993

INVENTOR(S) :  Joseph M. Beaurline and Robert K. Schultz

It is certified that error appears in the above-identified patent and that said Letters Patent is hereby corrected as shown below:

On title page, item [75] add the following; --Robert K. Schultz--

Signed and Sealed this

Sixteenth Day of August, 1994

Attest:

BRUCE LEHMAN

Attesting Officer

Commissioner of Patents and Trademarks